(12) United States Patent
Collier et al.

(10) Patent No.: US 7,585,336 B2
(45) Date of Patent: *Sep. 8, 2009

(54) FUEL ADDITIVE COMPOSITIONS FOR DIESEL ENGINE EQUIPPED WITH A PARTICULATE TRAP

(75) Inventors: Philip E. Collier, Oxfordshire (GB); Rinaldo Caprotti, Oxfordshire (GB)

(73) Assignee: Infineum International Limited (GB)

( * ) Notice: Subject to any disclaimer, the term of this patent is extended or adjusted under 35 U.S.C. 154(b) by 258 days.

This patent is subject to a terminal disclaimer.

(21) Appl. No.: 10/384,956

(22) Filed: Mar. 10, 2003

(65) Prior Publication Data

US 2003/0221362 A1    Dec. 4, 2003

(30) Foreign Application Priority Data

Mar. 13, 2002  (EP)  ................... 02251757

(51) Int. Cl.
*C10L 1/30*   (2006.01)
*C10L 1/18*   (2006.01)

(52) U.S. Cl. ............... 44/358; 44/363; 44/385

(58) Field of Classification Search ........... 44/358, 44/362, 363, 365, 366, 385
See application file for complete search history.

(56) References Cited

U.S. PATENT DOCUMENTS

| | | | | |
|---|---|---|---|---|
| 3,345,199 A * | 10/1967 | Fitch | ............... | 427/229 |
| 3,658,568 A * | 4/1972 | Donley | ............... | 427/165 |
| 3,762,890 A | 10/1973 | Collins | ............... | 44/66 |
| 4,257,913 A | 3/1981 | Fischer | ............... | 252/356 |
| 4,474,579 A | 10/1984 | Wilderson et al. | ............... | 44/57 |
| 4,505,718 A * | 3/1985 | Dorer, Jr. | ............... | 44/363 |
| 4,786,326 A * | 11/1988 | Grove | ............... | 106/15.05 |
| 5,145,488 A | 9/1992 | Weber et al. | ............... | 44/363 |
| 5,461,172 A * | 10/1995 | Cells | ............... | 556/49 |

FOREIGN PATENT DOCUMENTS

| | | |
|---|---|---|
| EP | 0 087 073 A2 | 8/1983 |
| EP | 0 188 115 A1 | 7/1986 |
| EP | 0 188 116 A1 | 7/1986 |
| EP | 0 199 558 A2 | 10/1986 |
| EP | 0 420 034 A1 | 4/1991 |
| EP | 0 575 189 A1 | 12/1993 |
| FR | 2 495 180 | 6/1982 |
| WO | WO97/04045 A1 | 2/1997 |

\* cited by examiner

*Primary Examiner*—Cephia D Toomer

(57) ABSTRACT

A fuel additive composition comprising a solution or dispersion of an oil soluble metal carboxylate or metal complex derived from a compound of the formula:

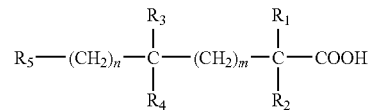

where $R_1$, $R_2$, $R_3$ and $R_4$ represent hydrogen or a hydrocarbyl having 1-30 carbon atoms ($C_1$-$C_{30}$), but at least two of $R_1$, $R_2$, $R_3$ or $R_4$ are $C_1$-$C_{30}$ hydrocarbyl; $R_5$ is a hydrocarbyl having 1 to 120 carbon atoms and m and n may each be zero or an integer such that the total number of carbon atoms in the carboxylate is not more than 125.

7 Claims, No Drawings

FUEL ADDITIVE COMPOSITIONS FOR DIESEL ENGINE EQUIPPED WITH A PARTICULATE TRAP

This invention relates to novel fuel additive compositions. More particularly, this invention relates to metal carboxylate fuel additives which have been found highly effective in improving the quality of emissions from the combustion of fuel oils, particularly diesel fuels. These carboxylate additives are useful in reducing soot formation and the buildup of particulates in diesel exhaust and the flue systems of boilers and are especially effective in improving the performance of particulate traps which are used in the exhaust systems of diesel engines, amongst other uses.

Diesel engines equipped with particulate traps, mounted in the exhaust stream, to "trap" or collect particulates in the exhaust to prevent their emission to the atmosphere are expected to be in greater use in the next few years.

Diesel engines running without particulate traps emit unburned hydrocarbons (HC), carbon monoxide (CO), nitrogen oxides ($NO_x$), and particulates, all of which are subject to current or proposed regulation. The problems of controlling these pollutants are compounded because there is a trade-off between particulates and nitrogen oxides—when the combustion conditions are modified to favor low nitrogen oxides emissions, particulates are increased. Particulate traps are employed to reduce the severity of the particulate emissions.

It now appears that a combination of techniques, including diesel traps and systems that use nitrogen oxides, will be required to meet realistic clean air goals. This manner of reducing particulates will be necessary because the techniques available for $NO_x$ reduction, such as timing changes and exhaust gas recirculation, require a trade-off with particulates. The achievement of lower emissions of $NO_x$, unburned hydrocarbons, and carbon monoxide, while controlling particulates over reasonable periods of time, continues to present a technical challenge.

Diesel particulates, their effect and control, are at the center of much concern and controversy. Their chemistry and environmental impact present complex issues. Generally, the diesel particulate matter is principally solid particles of carbon and metal compounds with adsorbed hydrocarbons, sulfates and aqueous species. Among the adsorbed species are aldehydes and polycyclic aromatic hydrocarbons. Some of these organics have been reported to be potential carcinogens or mutagens. Unburned hydrocarbons are related to the characteristic diesel odor and include aldehydes such as formaldehyde and acrolein. The need to control nano-particles is likely to lead to mandates requiring traps.

Unfortunately, increasing the recovery of particulates simply by modifying trap design or size would increase the rate of back pressure buildup within the trap, which causes increased fuel consumption and poor driveability. Moreover, control of the various pollutants seems to be interrelated, with reduction of one sometimes increasing levels of another. By modifying combustion to achieve more complete oxidation, decreases can be achieved for pollutants resulting from incomplete combustion, but $NO_x$ is typically increased under these conditions.

It is clear that diesel traps (either catalyzed or uncatalyzed) will be required in order to control particulates, especially where efforts are made to control $NO_x$.

The use of diesel traps and the need to improve them has resulted in a great deal of research and a great number of patents and technical publications. The traps are typically constructed of metal or ceramic and are capable of collecting the particulates from the exhaust and withstanding the heat produced by oxidation of carbonaceous deposits which must be burned off at regular intervals.

This burning off, or regeneration, could occur by itself if the operating temperature of the trap were sufficiently high. However, in the typical situation, the exhaust temperature is not constantly high enough, and secondary measures such as electrically heating to raise the trap temperature or using a catalyst on the washcoat to reduce the combustion temperature of particulates, have not been fully successful.

The use of organometallic salts and complexes to improve the operation of diesel engine particulate traps is disclosed, for example, in U.S. Pat. No. 5,344,467 issued Sep. 6, 1994, which teaches the use of a combination of an organometallic complex and an antioxidant. The organometallic complex is soluble or dispersible in the diesel fuel and is derived from an organic compound containing at least two functional groups attached to a hydrocarbon linkage.

WO99/36488 published Jul. 22, 1999 discloses fuel additive compositions which contain at least one iron-containing fuel-soluble or fuel-dispersible species in synergistic combination with at least one alkaline earth group metal-containing fuel-soluble or fuel-dispersible species. This combination of metallic additives is said to improve the operation of the diesel particulate filter traps.

Also pertinent to the subject matter of this invention is U.S. Pat. No. 4,946,609 issued Aug. 7, 1990, which teaches the use of iron compounds such as ferrocene, ferrocene derivatives and iron salts of organic acids as additives for lubricating oils used for diesel engines. It is taught that the presence of the iron compounds in the lubricating oil facilitates the regeneration of the diesel particle filters.

WO94/11467 published May 26, 1994 teaches a method to improve the operation of diesel traps through the use of a fuel additive comprising fuel-soluble compositions of a platinum group metal in effective amounts to lower the emissions of unburned hydrocarbons and carbon monoxide from the trap. The platinum group metals comprise platinum, palladium, rhodium or iridium.

The present invention is based upon the discovery that metal salts or complexes of carboxylic acids provide solutions or dispersions in hydrocarbon solvents which are storage stable over a wide temperature range and which are effective in improving the operation of diesel engine particulate traps and more generally useful to control soot and particulate matter buildup in exhaust and flue systems for large engines and boilers.

In accordance with the present invention there have been discovered stable fuel additive compositions for use with fuel oils and especially in fuels for use in diesel engines equipped with particulate traps which comprise stable solutions or dispersions of an oil soluble metal carboxylate or metal complex derived from a compound of the formula

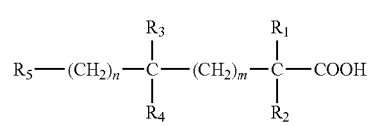

where $R_1$, $R_2$, $R_3$ and $R_4$ represent hydrogen or a hydrocarbyl having 1-30 carbon atoms ($C_1$-$C_{30}$), but at least two of $R_1$, $R_2$, $R_3$ or $R_4$ are $C_1$-$C_{30}$ hydrocarbyl; $R_5$ is a hydrocarbyl having 1 to 120 carbon atoms and m and n may each be zero or an integer such that the total number of carbon atoms in the carboxylate is not more than 125. The formula above is intended to represent a carboxylic acid which has at least two side chains of at least 1 to 30 carbon atoms in length, and preferably both $R_1$ and $R_2$ are hydrocarbyl so that the carboxylate is a neocarboxylate, i.e., having the carbon atom which is alpha to the carbonyl carbon connected to four other carbon atoms. The term hydrocarbyl is intended to apply to aromatic or aliphatic radicals composed principally of carbon and hydrogen, optionally substituted with oxygen or nitrogen, preferably aliphatic and particularly straight or branched chain alkyl or substituted alkyl, the substituents being nitrogen or oxygen. Most preferably the carboxylate is a neodecanoate.

Suitable examples of $R_5$ moieties are hydrocarbyl groups made from homo- or interpolymers (e.g. copolymers, terpolymers) of mono- and di-olefins having 2 to 10 carbon atoms, such as ethylene, propylene, 1-butene, isobutene, butadiene, isoprene, 1-hexene, 1-octene, etc. Typically, these olefins are 1-monoolefins. This hydrocarbyl can also be derived from the halogenated (e.g. chlorinated or brominated) analogs of such homo- or interpolymers or from polyethers.

The hydrocarbyl is predominantly saturated. The hydrocarbyl is predominantly aliphatic in nature, that is, containing no more than one non-aliphatic moiety (cycloalkyl, cycloalkenyl or aromatic) group of 6 or less carbon atoms for every 10 carbon atoms in the substituent. Usually, however, the hydrocarbyl contains no more than one such non-aliphatic group for every 50 carbon atoms, and in many cases, they contain no such non-aliphatic groups at all; that is, the typical substituents are purely aliphatic. Typically, these purely aliphatic hydrocarbyls are alkyl or alkenyl groups.

A preferred source of the $R_5$ moiety are poly(isobutene)s obtained by polymerization of a $C_4$ refinery stream having a butene content of 35 to 75 wt. % and isobutene content of 30 to 60 wt. % in the presence of a Lewis acid catalyst such as aluminum trichloride or boron trifluoride. These polybutenes predominantly contain monomer repeating units of the configuration $—C(CH_3)_2CH_2—$.

A wide variety of metals are suitable for forming the metal carboxylates or complexes useful as additives in the present invention. The metal may be an alkali metal, preferably Na, an alkaline earth metal, such as Ca, Mg or Sr, a Group IVB metal, especially Ti or Zr, a Group VIIIB metal, such as Mn, a Group VIII metal, particularly Ni, a Group IB metal, especially Cu, a Group IIB metal, such as Zn or any of the rare earth (lanthanide series of metals) metals having atomic numbers 57-71, especially cerium or mixtures of any of the foregoing metals. The most preferred metal is iron.

The additive solutions or dispersions will comprise 20-80% by weight of the carboxylate or complex and 80-20% by weight of hydrocarbon solvent. The term "additive solutions or dispersions" as used herein is meant to apply to both metal complexes and metal salts in hydrocarbon solvent.

Iron carboxylate salts are preferred. The iron salt may be Fe+2 or Fe+3 salts or a mixture thereof. The iron salt may also contain ferrous or ferric oxide, which results from the process used to prepare the neocarboxylic acid iron salt, which are known in the art as "overbased" when they contain oxide.

The metal salt or complex additive may also be acidic, that is, the metal carboxylate or metal complex additive salt composition may contain up to about 20% of unreacted free acid such as 1-20% by weight free acid, more preferably 0-10%, most preferably 0-5% free acid.

The metal carboxylate or complex additive of this invention may be overbased, acidic or neutral but preferably is neutral.

The salt may be neutral in that it contains a stoichiometric ratio of metal cations to carboxylate anions. It may also be acidic or overbased. Acidic salts contain an excess of carboxylic acid/carboxylate over that which would be considered stoichiometric and overbased salts contains an excess of metal species over the stoichiometric ratio. This excess metal may exist in one or a combination of forms including oxides, hydroxides or mixed oxidic salts. Lattice-like polynuclear-metal complexes may also be present.

For overbased salts, the excess metal may be introduced, either intentionally or unintentionally, during the main reaction process or alternatively may be introduced subsequent to this via post treatment. The elemental metal, oxides and hydroxides are common feedstocks for the overbasing process.

The solvent used to prepare the stable additive solutions or dispersions may generally be characterized as a normally liquid petroleum or synthetic hydrocarbon or oxygenated hydrocarbon or alcohol solvents, such as hexanol, 2-ethylhexanol or isodecyl alcohol solvent. Typical examples include kerosene, hydrotreated kerosene, isoparaffinic and paraffinic solvents and naphthenic aliphatic hydrocarbon solvents, aromatic solvents, dimers and higher oligomers of propylene, butene and similar olefins and mixtures thereof. Commercial products such as "Solvesso", "Varsol", "Norpar" and "Isopar" are suitable. Such solvents may also contain functional groups other than carbon and hydrogen provided such groups do not adversely affect the performance of the additive composition. Preferred are isoparaffinic and paraffinic hydrocarbon solvents. Preferably, the solvent has a flash point greater than 20° C., more preferably greater than 40° C., most preferably greater than 55° C.

The metal carboxylates or complexes of the present invention may be used as additives in a wide variety of fuel oils, particularly diesel fuel oils.

Such fuel oils include "middle distillate" fuel oil which refers to petroleum-based fuel oils obtainable in refining crude oil as the fraction from the light, kerosene or jet fuel, fraction to the heavy fuel oil fraction. These fuel oils may also comprise atmospheric or vacuum distillate, cracked gas oil or a blend, in any proportions, of straight run and thermally and/or catalytically cracked or hydrocracked distillate. Examples include hydrocracked streams, kerosene, jet fuel, diesel fuel, heating oil, visbroken gas oil, light cycle oil and vacuum gas oil. Such middle distillate fuel oils usually boil over a temperature range, generally within the range of 100° C. to 500° C., as measured according to ASTM D86, more especially between 150° C. and 400° C.

Also suitable is residual fuel oil used in marine diesel engines and stationary, railway, furnace and boiler applications.

Preferred vegetable-based fuel oils are triglycerides of monocarboxylic acids, for example, acids containing 10-25 carbon atoms, and typically have the general formula shown below

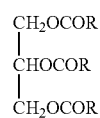

where R is an aliphatic radical of 10-25 carbon atoms which may be saturated or unsaturated.

Generally, such oils contain glycerides of a number of acids, the number and kind varying with the source vegetable of the oil.

Suitable fuel oils also include mixtures of 1-50% by weight of vegetable oils or methyl esters of fatty acids with petroleum based diesel fuel oils. Also suitable are fuels emulsified with water and alcohols, which contain suitable surfactants.

Examples of oils are rapeseed oil, coriander oil, soyabean oil, linseed oil, cottonseed oil, sunflower oil, castor oil, olive oil, peanut oil, maize oil, almond oil, palm kernel oil, coconut oil, mustard seed oil, beef tallow and fish oils. Rapeseed oil, which is a mixture of fatty acids partially esterified with glycerol, is preferred as it is available in large quantities and can be obtained in a simple way by pressing from rapeseed. Esters of tall oil fatty acids are also suitable as fuels.

Further preferred examples of vegetable-based fuel oils are alkyl esters, such as methyl esters, of fatty acids of the vegetable or animal oils. Such esters can be made by transesterification.

As lower alkyl esters of fatty acids, consideration may be given to the following, for example as commercial mixtures: the ethyl, propyl, butyl and especially methyl esters of fatty acids with 12 to 22 carbon atoms, for example of lauric acid, myristic acid, palmitic acid, palmitoleic acid, stearic acid, oleic acid, elaidic acid, petroselic acid, ricinoleic acid, elaeostearic acid, linoleic acid, linolenic acid, eicosanoic acid, gadoleic acid, docosanoic acid or erucic acid, which have an iodine number from 50 to 150, especially 90 to 125. Mixtures with particularly advantageous properties are those which contain mainly, i.e. to at least 50 wt %, such as 1-5 wt. % or 1-15 wt. % methyl esters of fatty acids with 16 to 22 carbon atoms and 1, 2 or 3 double bonds. The preferred lower alkyl esters of fatty acids are the methyl esters of oleic acid, linoleic acid, linolenic acid and erucic acid.

Commercial mixtures of the stated kind are obtained for example by cleavage and esterification of natural fats and oils by their transesterification with lower aliphatic alcohols. For production of lower alkyl esters of fatty acids it is advantageous to start from fats and oils with high iodine number, such as, for example, palmoil, linseed oil, tall oil, sunflower oil, rapeseed oil, coriander oil, castor oil, soyabean oil, cottonseed oil, peanut oil or beef tallow. Lower alkyl esters of fatty acids based on a new variety of rapeseed oil, the fatty acid component of which is derived to more than 80 wt % from unsaturated fatty acids with 18 carbon atoms, are preferred.

Most preferred as a vegetable-based fuel oil is rapeseed methyl ester.

The inventive fuel oil compositions, preferably diesel fuel compositions, contain an effective amount of one or more of the metal carboxylates or complexes described above to lower the ignition temperature of exhaust particulates formed on burning of the diesel fuel. The concentration of these metal carboxylates or complexes in the inventive fuels is usually expressed in terms of the level of addition of the metal from such carboxylates. These fuels contain at least 1 part to 25 parts of metal per million parts (ppm) by weight of fuel, preferably from about 2 to about 10 parts of metal per million parts of fuel, and most preferably 5 to about 10 parts of metal per million parts by weight of fuel.

The inventive diesel fuel compositions can contain, in addition to the above-indicated metal carboxylates or complexes, other additives which are well known to those of skill in the art. These include dyes, cetane improvers, rust inhibitors such as alkylated succinic acids and anhydrides, bacteriostatic agents, gum inhibitors, metal deactivators, demulsifiers, upper cylinder lubricants and anti-icing agents, antioxidants and antistatic additives.

The metal additive of this invention may also be used in combination with the various lubricity additives which are now commonly used in low sulfur fuels. Such lubricity additives include monohydric or polyhydric alcohol esters of $C_2$-$C_{50}$ carboxylic acids such as glycerol monooleate, esters of polybasic acids with $C_1$-$C_5$ monohydric alcohols, esters of dimerized carboxylic acids, reaction products of polycarboxylic acids and epoxides such as 1,2-epoxyethane and 1,2-epoxypropane and lubricity additives derived from fatty acids such as vegetable oil fatty acid methyl esters.

Further examples are lubricity additives prepared by combining the aforesaid esters of $C_2$-$C_{50}$ carboxylic acids with an ashless dispersant comprising an acylated nitrogen compound having a hydrocarbyl substituent of at least 10 carbon atoms made by reacting an acylating agent with an amino compound, such as the reaction products of polyisobutenyl ($C_{50}$-$C_{500}$) succinic anhydride with ethylene polyamines having 3 to 7 amino nitrogen atoms.

Other lubricity additives are combinations of the aforesaid esters with ethylene-unsaturated ester copolymers having, in addition to units derived from ethylene, units of the formula

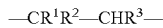

wherein $R^1$ represents hydrogen or methyl; $R^2$ represents $COOR^4$, wherein $R^4$ represents an alkyl group having from 1 to 9 carbon atoms which is straight chain or, if it contains 2 or more carbon atoms, branched, or $R^2$ represents $OOCR^5$, wherein $R^5$ represents $R^4$ or H; and $R^3$ represents H or $COOR^4$. Examples are ethylene-vinyl acetate and ethylene-vinyl propionate and other copolymers where there is present 5-40% of the vinyl ester.

Other lubricity additives are hydroxy amines of the formula

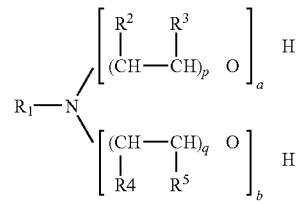

where R1 is an alkenyl radical having one or more double bonds or an alkyl radical and containing from 4 to 50 carbon atoms, or a radical of the formula

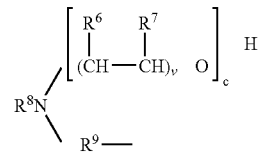

where each of $R^2$, $R^3$, $R^4$, $R^5$, $R^6$ and $R^7$ is independently hydrogen or a lower alkyl radical; $R^8$ is an alkenyl radical having one or more double bonds or an alkyl radical and containing from 4 to 50 carbon atoms; $R^9$ is an alkylene radical containing from 2 to 35, e.g. 2 to 6, carbon atoms; each of p, q and v is an integer between 1 and 4; and each of a, b and c may be O, providing that at least one of a, b or c is an integer between 1 and 75.

The metal carboxylate or complex additive of the invention may also be used in combination with other diesel performance additives such as (i) the reaction products of hydrocarbyl-substituted succinic acylating agents, the hydrocarbyl having a Mn of 250-2500 and one or more polyalkylene polyamines, especially triethylene tetramine or polyamines having 35% or more polyamines having more than 6 N atoms per molecule, (ii) polyalkylene amine detergents which are derived from polyalkylenes of greater than 250 mass units, which are themselves preferably derived from $C_{2-10}$ alkenes and more preferably from butene and/or iso-butene. The are prepared by linking ammonia, amines, polyamines, alkylamines or alkanolamines to and/or between these polymers. A variety of methods can be used to achieve this, for example, routes via chlorination, hydroformylation, epoxidation and ozonolysis are know in the art. Typical examples, which are also well known in the art, are polyisobutene monoamine ("PIBA") and polyisobutene-ethylenediamine ("PIB-EDA"). Further examples are described in EP244616 and WO 98/28346, (iii) silicon-containing anti-foam agents such as siloxane block copolymers or (iv) cetane improvers such as 2-ethyl hexyl nitrate.

The metal carboxylate or complex additives of this invention may also be used in combination with cold flow additives such as an oil-soluble hydrogenated block diene polymer, comprising at least one crystallizable block, obtainable by end-to-end polymerization of a linear diene, and at least one non-crystallizable block, the non-crystallizable block being obtainable by 1,2-configuration polymerization of a linear diene, by polymerization of a branched diene, or by a mixture of such polymerizations, or another cold flow improver as defined in (A)-(F) below.

(A) An ethylene-unsaturated ester copolymer, more especially one having, in addition to units derived from ethylene, units of the formula

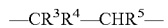

wherein $R^3$ represents hydrogen or methyl, $R^4$ represents $COOR^6$, wherein $R^6$ represents an alkyl group having from 1 to 9 carbon atoms, which is straight chain or, if it contains 3 or more carbon atoms, branched, or $R^4$ represents $OOCR^7$, wherein $R^7$ represents $R^6$ or H, and $R^5$ represents H or $COOR^6$. Also suitable are terpolymers and tetrapolymers such as ethyl vinyl 2-ethyl hexanoate vinyl acetate.

These may comprise a copolymer of ethylene with an ethylenically unsaturated ester, or derivatives thereof. An example is a copolymer of ethylene with an ester of a saturated alcohol and an unsaturated carboxylic acid, but preferably the ester is one of an unsaturated alcohol with a saturated carboxylic acid. An ethylene-vinyl ester copolymer is advantageous; an ethylene-vinyl acetate, ethylene-vinyl propionate, ethylene-vinyl 2-ethyl hexanoate, or ethylene-vinyl octanoate copolymer is preferred.

As disclosed in U.S. Pat. No. 3,961,916, flow improver compositions may comprise a wax growth arrestor and a nucleating agent. This arrestor may, for example, be an ethylene-unsaturated ester as described above, especially an ethylene vinyl acetate with a molecular weight (Mn, measured by gel permeation chromatography against a polystyrene standard) of at most 14000, advantageously at most 10000, preferably 2000 to 6000, and more preferably from 2000 to 5500, and an ester content of 7.5% to 35%, preferably from 10 to 20, and more preferably from 10 to 17, molar percent.

It is within the scope of the invention to include an additional nucleator, e.g., an ethylene-unsaturated ester, especially vinyl acetate, copolymer having a number average molecular weight in the range of 1200 to 20000, and a vinyl ester content of 0.3 to 10, advantageously 3.5 to 7.0 molar per cent.

(B) A comb polymer.

Such polymers are polymers in which branches containing hydrocarbyl groups are pendant from a polymer backbone, and are discussed in "Comb-Like Polymers. Structure and Properties", N. A. Platé and V. P. Shibaev, J. Poly. Sci. Macromolecular Revs., 8, p 117 to 253 (1974).

Generally, comb polymers have one or more long chain hydrocarbyl branches, e.g., oxyhydrocarbyl branches, normally having from 10 to 30 carbon atoms, pendant from a polymer backbone, said branches being bonded directly or indirectly to the backbone. Examples of indirect bonding include bonding via interposed atoms or groups, which bonding can include covalent and/or electrovalent bonding such as in a salt.

Advantageously, the comb polymer is a homopolymer having, or a copolymer at least 25 and preferably at least 40, more preferably at least 50, molar percent of the units of which have, side chains containing at least 6, and preferably at least 10, atoms.

As examples of preferred comb polymers there may be mentioned those of the general formula

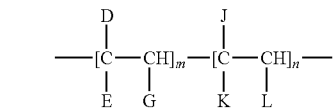

wherein $D=R^{11}$, $COOR^{11}$, $OCOR^{11}$, $R^{12}COOR^{11}$, or $OR^{11}$,
  $E=H$, $CH_3$, D, or $R^{12}$,
  $G=H$ or D
  $J=H$, $R^{12}$, $R^{12}COOR^{11}$, or an aryl or heterocyclic group,
  $K=H$, $COOR^{12}$, $OCOR^{12}$, $OR^{12}$ or COOH,
  $L=H$, $R^{12}$, $COOR^{12}$, $OCOR^{12}$, COOH, or aryl,
  $R^{11} \geq C_{10}$ hydrocarbyl,
  $R^{12} \geq C_1$ hydrocarbyl or hydrocarbylene, and m and n represent mole fractions, m being finite and preferably within the range of from 1.0 to 0.4, n being less than 1 and preferably in the range of from 0 to 0.6.

$R^{11}$ advantageously represents a hydrocarbyl group with from 10 to 30 carbon atoms, while $R^{12}$ advantageously represents a hydrocarbyl or hydrocarbylene group with from 1 to 30 carbon atoms.

The comb polymer may contain units derived from other monomers if desired or required.

These comb polymers may be copolymers of maleic anhydride or fumaric or itaconic acids and another ethylenically unsaturated monomer, e.g., an (α-olefin, including styrene, or an unsaturated ester, for example, vinyl acetate or homopolymer of fumaric or itaconic acids. It is preferred but not essential that equimolar amounts of the comonomers be used although molar proportions in the range of 2 to 1 and 1 to 2 are suitable. Examples of olefins that may be copolymerized with e.g., maleic anhydride, include 1-decene, 1-dodecene, 1-tetradecene, 1-hexadecene, and 1-octadecene.

The acid or anhydride group of the comb polymer may be esterified by any suitable technique and although preferred it is not essential that the maleic anhydride or fumaric acid be at least 50% esterified. Examples of alcohols which may be used include n-decan-1-ol, ndodecan-1-ol, n-tetradecan-1-ol, n-hexadecan-1-ol, and noctadecan-1-ol. The alcohols may also include up to one methyl branch per chain, for example, 1-methylpentadecan1-ol or 2-methyltridecan-1-ol. The alcohol may be a mixture of normal and single methyl branched alcohols.

It is preferred to use pure alcohols rather than the commercially available alcohol mixtures but if mixtures are used the $R^{12}$ refers to the average number of carbon atoms in the alkyl group; if alcohols that contain a branch at the 1 or 2 positions are used $R^{12}$ refers to the straight chain backbone segment of the alcohol.

These comb polymers may especially be fumarate or itaconate polymers and copolymers such for example as those described in EP-A-153176, EP-A-153177 and -EP-A-225688, and WO 91/16407.

Particularly preferred fumarate comb polymers are copolymers of alkyl fumarates and vinyl acetate, in which the alkyl groups have from 12 to 20 carbon atoms, more especially polymers in which the alkyl groups have 14 carbon atoms or in which the alkyl groups are a mixture of $C_{14}/C_{16}$ alkyl groups, made, for example, by solution copolymerizing an equimolar mixture of fumaric acid and vinyl acetate and reacting the resulting copolymer with the alcohol or mixture of alcohols, which are preferably straight chain alcohols. When the mixture is used it is advantageously a 1:1 by weight mixture of normal $C_{14}$ and $C_{16}$ alcohols. Furthermore, mixtures of the $C_{14}$ ester with the mixed $C_{14}/C_{16}$ ester may advantageously be used. In such mixtures, the ratio of $C_{14}$ to $C_{14}/C_{16}$ is advantageously in the range of from 1:1 to 4:1, preferably 2:1 to 7:2, and most preferably about 3:1, by weight. The particularly preferred comb polymers are those having a number average molecular weight, as measured by vapour phase osmometry, of 1,000 to 100,000, more especially 1,000 to 30,000.

Other suitable comb polymers are the polymers and copolymers of α-olefins and esterified copolymers of styrene and maleic anhydride, and esterified copolymers of styrene and fumaric acid; mixtures of two or more comb polymers may be used in accordance with the invention and, as indicated above, such use may be advantageous. Other examples of comb polymers are hydrocarbon polymers, e.g., copolymers of ethylene and at least one α-olefin, the a-olefin preferably having at most 20 carbon atoms, examples being n-decene-1 and n-dodecene-1. Preferably, the number average molecular weight of such a copolymer is at least 30,000 measured by GPC. The hydrocarbon copolymers may be prepared by methods known in the art, for example using a Ziegler type catalyst.

(C) Polar nitrogen compounds.

Such compounds are oil-soluble polar nitrogen compounds carrying one or more, preferably two or more, substituents of the formula >$NR^{13}$, where $R^{13}$ represents a hydrocarbyl group containing 8 to 40 atoms, which substituent or one or more of which substituents may be in the form of a cation derived therefrom. The oil soluble polar nitrogen compound is generally one capable of acting as a wax crystal growth inhibitor in fuels it comprises for example one or more of the following compounds:

An amine salt and/or amide formed by reacting at least, one molar proportion of a hydrocarbyl-substituted amine with a molar proportion of a hydrocarbyl acid having from 1 to 4 carboxylic acid groups or its anhydride, the substituent(s) of formula >$NR^{13}$ being of the formula $-NR^{13}R^{14}$ where $R^{13}$ is defined as above and $R^{14}$ represents hydrogen or $R^{13}$, provided that $R^{13}$, and $R^{14}$ may be the same or different, said substituents constituting part of the amine salt and/or amide groups of the compound.

Ester/amides may be used, containing 30 to 300, preferably 50 to 150, total carbon atoms. These nitrogen compounds are described in U.S. Pat. No. 4,211,534. Suitable amines are predominantly $C_{12}$ to $C_{40}$ primary, secondary, tertiary or quaternary amines or mixtures thereof but shorter chain amines may be used provided the resulting nitrogen compound is oil soluble, normally containing about 30 to 300 total carbon atoms. The nitrogen compound preferably contains at least one straight chain $C_8$ to $C_{40}$, preferably $C_{14}$ to $C_{24}$, alkyl segment.

Suitable amines include primary, secondary, tertiary or quaternary, but are preferably secondary. Tertiary and quaternary amines only form amine salts. Examples of amines include tetradecylamine, cocoamine, and hydrogenated tallow amine. Examples of secondary amines include dioctacedyl amine and methylbehenyl amine. Amine mixtures are also suitable such as those derived from natural materials. A preferred amine is a secondary hydrogenated tallow amine, the alkyl groups of which are derived from hydrogenated tallow fat composed of approximately 4% $C_{14}$, 31% $C_{16}$, and 59% $C_{18}$.

Examples of suitable carboxylic acids and their anhydrides for preparing the nitrogen compounds include ethylenediamine tetraacetic acid, and carboxylic acids based on cyclic skeletons, e.g., cyclohexane-1,2-dicarboxylic acid, cyclohexene-1,2-dicarboxylic acid, cyclopentane-1,2-dicarboxylic acid and naphthalene dicarboxylic acid, and 1,4-dicarboxylic acids including dialkyl spirobislactones. Generally, these acids have about 5 to 13 carbon atoms in the cyclic moiety. Preferred acids useful in the present invention are benzene dicarboxylic acids e.g., phthalic acid, isophthalic acid, and terephthalic acid. Phthalic acid and its anhydride are particularly preferred. The particularly preferred compound is the amide-amine salt formed by reacting 1 molar portion of phthalic anhydride with 2 molar portions of dihydrogenated tallow amine. Another preferred compound is the diamide formed by dehydrating this amide-amine salt.

Other examples are long chain alkyl or alkylene substituted dicarboxylic acid derivatives such as amine salts of monoamides of substituted succinic acids, examples of which are known in the art and described in U.S. Pat. No. 4,147,520, for example. Suitable amines may be those described above.

Other examples are condensates, for example, those described in EP-A-327427.

(D) A compound containing a cyclic ring system carrying at least two substituents of the general formula below on the ring system

where A is a linear or branched chain aliphatic hydrocarbylene group optionally interrupted by one or more hetero atoms, and $R^{15}$ and $R^{16}$ are the same or different and each is independently a hydrocarbyl group containing 9 to 40 atoms optionally interrupted by one or more hetero atoms, the substituents being the same or different and the compound optionally being in the form of a salt thereof. Advantageously, A has from 1 to 20 carbon atoms and is preferably a methylene or polymethylene group. Such compounds are described in WO 93/04148 and WO94/07842.

(E) A hydrocarbon polymer.

Examples of suitable hydrocarbon polymers are those of the general formula

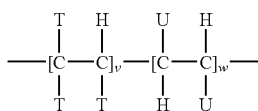

wherein T=H or $R^{21}$ wherein
   $R^{21}$=$C_1$ to $C_{40}$ hydrocarbyl, and
   U=H, T, or aryl and v and w represent mole fractions, v being within the range of from 1.0 to 0.0, w being in the range of from 0.0 to 1.0.

Examples of hydrocarbon polymers are disclosed in WO 91/11488.

Preferred copolymers are ethylene α-olefin copolymers, having a number average molecular weight of at least 30,000. Preferably the α-olefin has at most 28 carbon atoms. Examples of such olefins are propylene, 1-butene, isobutene, n-octene-1, isooctene-1, n-decene-1, and n-dodecene-1. The copolymer may also comprise small amounts, e.g., up to 10% by weight, of other copolymerizable monomers, for example olefins other than α-olefins, and non-conjugated dienes. The preferred copolymer is an ethylene-propylene copolymer.

The number average molecular weight of the ethylene α-olefin copolymer is, as indicated above, preferably at least 30,000, as measured by gel permeation chromatography (GPC) relative to polystyrene standards, advantageously at least 60,000 and preferably at least 80,000. Functionally no upper limit arises but difficulties of mixing result from increased viscosity at molecular weights above about 150,000, and preferred molecular weight ranges are from 60,000 and 80,000 to 120,000.

Advantageously, the copolymer has a molar ethylene content between 50 and 85 per cent. More advantageously, the ethylene content is within the range of from 57 to 80%, and preferably it is in the range from 58 to 73%; more preferably from 62 to 71%, and most preferably 65 to 70%.

Preferred ethylene-α-olefin copolymers are ethylenepropylene copolymers with a molar ethylene content of from 62 to 71% and a number average molecular weight in the range 60,000 to 120,000; especially preferred copolymers are ethylene-propylene copolymers with an ethylene content of from 62 to 71% and a molecular weight from 80,000 to 100,000.

The copolymers may be prepared by any of the methods known in the art, for example using a Ziegler type catalyst. The polymers should be substantially amorphous, since highly crystalline polymers are relatively insoluble in fuel oil at low temperatures.

Other suitable hydrocarbon polymers include a low molecular weight ethylene-α-olefin copolymer, advantageously with a number average molecular weight of at most 7500, advantageously from 1,000 to 6,000, and preferably from 2,000 to 5,000, as measured by vapour phase osmometry. Appropriate α-olefins are as given above, or styrene, with propylene again being preferred. Advantageously the ethylene content is from 60 to 77 molar per cent, although for ethylene-propylene copolymers up to 86 molar per cent by weight ethylene may be employed with advantage.

(F) A polyoxyalkylene compound.

Examples are polyoxyalkylene esters, ethers, ester/ethers and mixtures thereof, particularly those containing at least one, preferably at least two, $C_{10}$ to $C_{30}$ linear alkyl groups and a polyoxyalkylene glycol group of molecular weight up to 5,000, preferably 200 to 5,000, the alkyl group in said polyoxyalkylene glycol containing from 1 to 4 carbon atoms. These materials form the subject of EP-A-0061895. Other such additives are described in U.S. Pat. No. 4,491,455.

The preferred esters, ethers or ester/ethers are those of the general formula

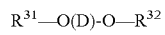

where $R^{31}$ and $R^{32}$ may be the same or different and represent
(a) n-alkyl-
(b) n-alkyl-CO—
(c) n-alkyl-O—CO($CH_2$)$_x$- or
(d) n-alkyl-O—CO($CH_2$)$_x$—CO— x being, for example, 1 to 30, the alkyl group being linear and containing from 10 to 30 carbon atoms, and D representing the polyalkylene segment of the glycol in which the alkylene group has 1 to 4 carbon atoms, such as a polyoxymethylene, polyoxyethylene or polyoxytrimethylene moiety which is substantially linear; some degree of branching with lower alkyl side chains (such as in polyoxypropylene glycol) may be present but it is preferred that the glycol is substantially linear. D may also contain nitrogen.

Examples of suitable glycols are substantially linear polyethylene glycols (PEG) and polypropylene glycols (PPG) having a molecular weight of from 100 to 5,000, preferably from 200 to 2,000. Esters are preferred and fatty acids containing from 10-30 carbon atoms are useful for reacting with the glycols to form the ester additives, it being preferred to use a $C_{18}$-$C_{24}$ fatty acid, especially behenic acid. The esters may also be prepared by esterifying polyethoxylated fatty acids or polyethoxylated alcohols.

Polyoxyalkylene diesters, diethers, ether/esters and mixtures thereof are suitable as additives, diesters being preferred for use in narrow boiling distillates, when minor amounts of monoethers and monoesters (which are often formed in the manufacturing process) may also be present. It is preferred that a major amount of the dialkyl compound be present. In particular, stearic or behenic diesters of polyethylene glycol, polypropylene glycol or polyethylene/polypropylene glycol mixtures are preferred.

Other examples of polyoxyalkylene compounds are those described in Japanese Patent Publication Nos. 2-51477 and 3-34790, and the esterified alkoxylated amines described in EP-A-117108 and EP-A-326356.

In one embodiment of the invention the metal carboxylate or complex solution or dispersion is combined with the diesel fuel by direct addition, or as part of a concentrate as discussed above or in admixtures with other fuel additives as disclosed herein, and the diesel fuel is used to operate a diesel engine equipped with an exhaust system particulate trap. The diesel fuel containing the additive is contained in a fuel tank, transmitted to the diesel engine where it is burned, and the metal salt reduces the ignition temperature of exhaust particles collected in the exhaust system particulate trap. In another embodiment, the foregoing operational procedure is used except that the additive solution is maintained on board the apparatus being powered by the diesel engine (e.g., automobile, bus, truck, etc.) in a separate fuel additive dispenser apart from the diesel fuel. The additive solution or dispersion is combined or blended with the diesel fuel during re-filling of the diesel fuel tank. In this latter embodiment, the additive solution or dispersion is maintained in the fuel additive dispenser and can form a part of a fuel additive concentrate of the concentrate being combined with the diesel fuel. Other techniques comprise adding the metal carboxylate or complex additive into the intake or exhaust manifold or adding the additive to the fuel at fuel depots prior to filling the tank of the diesel powered vehicle.

A further embodiment of this invention is the use of the metal carboxylates or complexes as additives for heavy fuel oil which is used for example in railroad, power generation and marine type applications which employ large engines and boilers or furnaces.

The heavy fuel may in particular have one or more of the following characteristics:
(i) a 95% distillation point (ASTM D86) of greater than 330° C., preferably greater than 360° C., more preferably greater than 400° C., and most preferably greater than 430° C.,
(ii) a cetane number (measured by ASTM D613) of less than 53, preferably less than 49, more preferably less than 45;
(iii) an aromatic content of greater than 15% wt., preferably greater than 25% and more preferably greater than 40%; and Typically, marine fuels accord with the standard specification ASTM D-2069 and may be either distillate or residual fuels as described within that specification, and may in particular have sulphur contents of greater than 0.05%, preferably greater than 0.1%, more preferably greater than 0.2% by weight, and a kinematic viscosity of 40° C. in cSt of at least 1.40.

EXAMPLES

A series of iron compounds in hydrocarbon solvents at varying concentrations were subjected to stability tests by being stored at temperatures of from −30° C. to +40° C. for up to 180 days. The results show that only iron neocarboxylate compounds exhibited the requisite stability. Iron oleate (colloidal), iron 2-ethylhexanoate and iron cyclopentadienyl (ferrocene) failed after one day across all temperature ranges. Results are in the following table. Phase separation and loss of homogeneity was recorded as a failure.

TABLE

Stability Tests

| wt. % Iron in Compound | Iron Compound | Concentration, wt. % | wt. % Iron in Final Product | Stability at −30° C. | Stability at −20° C. | Stability at −10° C. | Stability at 0° C. | Stability at 20° C. | Stability at 40° C. |
|---|---|---|---|---|---|---|---|---|---|
| 14 | Iron Oleate | 20 | 2.8 | Failed after 1 day | Failed after 1 day | Failed after 1 day | Failed after 1 day | Failed after 1 day | Failed after 1 day |
| 14 | Overbased | 40 | 5.6 | Failed after 1 day | Failed after 1 day | Failed after 1 day | Failed after 1 day | Failed after 1 day | Failed after 1 day |
| 14 | | 60 | 8.4 | Failed after 1 day | Failed after 1 day | Failed after 1 day | Failed after 1 day | Failed after 1 day | Failed after 1 day |
| 14 | | 80 | 11.2 | Failed after 1 day | Failed after 1 day | Failed after 1 day | Failed after 1 day | Failed after 1 day | Failed after 1 day |
| 6 | Iron 2-ethylhexanoate | 20 | 1.2 | Failed after 1 day | Failed after 1 day | Failed after 1 day | Failed after 1 day | Failed after 1 day | Failed after 7 day |
| 6 | | 40 | 2.4 | Failed after 1 day | Failed after 1 day | Failed after 1 day | Failed after 1 day | Failed after 1 day | Failed after 7 day |
| 6 | | 60 | 3.6 | Failed after 1 day | Failed after 1 day | Failed after 1 day | Failed after 1 day | Failed after 1 day | Failed after 1 day |
| 6 | | 80 | 4.8 | Failed after 1 day | Failed after 1 day | Failed after 1 day | Failed after 1 day | Failed after 1 day | Failed after 1 day |
| 30 | Ferrocene | 1 | 0.3 | Failed after 1 day | Failed after 1 day | Failed after 1 day | Failed after 1 day | Failed after 1 day | Failed after 7 day |
| 30 | | 5 | 1.5 | Failed after 1 day | Failed after 1 day | Failed after 1 day | Failed after 1 day | Failed after 1 day | Failed after 7 day |
| 6 | Iron Neodecanoate | 40 | 2.4 | Pass after 180 days | Pass after 180 days | Pass after 180 days | Pass after 180 days | Pass after 180 days | Pass after 180 days |

(iv) a Ramsbottom carbon residue (by ASTM D524) of greater than 0.01% mass, preferably greater than 0.15% mass, more preferably greater than 0.3% mass, such as 1% or 5% mass, and most preferably greater than 10% mass.

As defined earlier, marine diesel fuels may in particular contain streams such as streams produced from fluid catalytic cracking. Such materials usually having a density @ 15° C. of 900 to 970 kg/m³ and characterised by low cetane number values, typically ranging from 10 or lower to around 30 to 35; from thermal cracking processes, like visbreaking and coking. Such streams typically having a density range @ 15° C. of 830 to 930 kg/m³ and a cetane value of 20 to 50; and from hydrocracking that uses severe conditions, e.g. temperature in excess of 400° C. coupled with pressures of 130 bars or greater, to produce streams characterized by cetane number from 45 to 60 and having a density range @ 15° C. from 800 to 860 kg/m³.

The invention claimed is:
1. A method of improving the operation of a diesel engine equipped with a trap for particulate emissions in the diesel engine exhaust comprising: providing a diesel fuel to the engine comprising a solution or dispersion of an oil soluble metal neocarboxylate or metal complex derived from a compound of the formula:

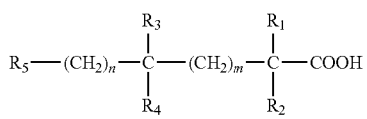

where $R_1$ and $R_2$ are a hydrocarbyl having 1-30 carbon atoms, $R_3$ and $R_4$ represent hydrogen or a hydrocarbyl having 1-30 carbon atoms; $R_5$ is a hydrocarbyl having 1 to 120 carbon atoms and m and n may each be zero or an integer such that the total number of carbon atoms in the neocarboxylate is not more than 125, the solution comprising 20-80% by weight of the neocarboxylate or complex and 80-20% by weight of a hydrocarbon solvent.

2. The method of claim 1 wherein the metal is alkali metal, alkaline earth metal, Group IVB metal, Group VIIIB metal, Group VIII metal, Group IB metal, Group IIB metal or a rare earth metal or a mixture of such metals.

3. The method of claim 1 wherein $R_1$ and $R_2$ are both hydrocarbyl and $R_3$ and $R_4$ are hydrogen.

4. The method of claim 1 wherein the metal is iron or cerium.

5. The method of claim 2 wherein the metal is iron or cerium.

6. The method of claim 5 wherein the neocarboxylate is neodecanoate.

7. The method of claim 1 wherein the solvent is a paraffinic or isoparaffinic hydrocarbon solvent.

* * * * *